(12) United States Patent
Kostov

(10) Patent No.: US 11,771,354 B2
(45) Date of Patent: Oct. 3, 2023

(54) DEVICE AND METHOD FOR MONITORING IRREGULAR LIQUID FLOW RATES

(71) Applicant: Konstantin Kostov, Chicago, IL (US)

(72) Inventor: Konstantin Kostov, Chicago, IL (US)

(*) Notice: Subject to any disclaimer, the term of this patent is extended or adjusted under 35 U.S.C. 154(b) by 565 days.

(21) Appl. No.: 15/317,226

(22) PCT Filed: Jun. 12, 2015

(86) PCT No.: PCT/US2015/035703
§ 371 (c)(1),
(2) Date: Dec. 8, 2016

(87) PCT Pub. No.: WO2015/192108
PCT Pub. Date: Dec. 17, 2015

(65) Prior Publication Data
US 2017/0100068 A1    Apr. 13, 2017

Related U.S. Application Data

(60) Provisional application No. 62/011,111, filed on Jun. 12, 2014.

(51) Int. Cl.
| | | |
|---|---|---|
| *A61B 5/20* | (2006.01) |
| *A61B 5/00* | (2006.01) |
| *A61B 10/00* | (2006.01) |
| *A61J 1/10* | (2006.01) |
| *A61J 1/18* | (2023.01) |
| *A61M 25/00* | (2006.01) |
| *A61M 39/28* | (2006.01) |
| *A61F 5/441* | (2006.01) |

(52) U.S. Cl.
CPC ............. *A61B 5/208* (2013.01); *A61B 5/742* (2013.01); *A61B 5/746* (2013.01); *A61B 10/007* (2013.01); *A61F 5/441* (2013.01); *A61J 1/10* (2013.01); *A61J 1/18* (2013.01); *A61M 25/0017* (2013.01); *A61M 39/28* (2013.01); *A61J 2200/76* (2013.01)

(58) Field of Classification Search
CPC ......... A61B 5/208; A61B 5/742; A61B 5/746; A61B 10/007; A61F 5/441; A61J 1/10; A61J 1/18; A61J 2200/76; A61M 25/0017; A61M 39/28
See application file for complete search history.

(56) References Cited

U.S. PATENT DOCUMENTS

| | | | | |
|---|---|---|---|---|
| 7,739,907 B2* | 6/2010 | Boiarski | ............... | A61F 5/4404 |
| | | | | 73/149 |
| 2005/0256447 A1* | 11/2005 | Richardson | ....... | A61M 5/16813 |
| | | | | 604/65 |

(Continued)

*Primary Examiner* — Nicholas J. Weiss
*Assistant Examiner* — Gabriella E Burnette
(74) *Attorney, Agent, or Firm* — Verrill Dana, LLP

(57) ABSTRACT

A device for monitoring of an irregular liquid flow rate, such as urine or another bodily fluid from a catheterized patient, includes a measurement chamber having an inlet and an outlet, a liquid level sensor in the collection vessel, a closure, and a control unit. The chamber is configured to allow liquid to enter through the inlet and leave through the outlet, respectively. The closure opens and closes the outlet in response to signals from the control unit. The liquid level sensor provides a signal to the control unit when liquid in the vessel attains a first preset volume.

23 Claims, 8 Drawing Sheets

(56) References Cited

U.S. PATENT DOCUMENTS

| | | | |
|---|---|---|---|
| 2006/0052764 A1* | 3/2006 | Gelfand | A61B 5/201 |
| | | | 604/500 |
| 2006/0100743 A1 | 5/2006 | Townsend et al. | |
| 2007/0106177 A1 | 5/2007 | Hama | |
| 2009/0314101 A1 | 12/2009 | Levine | |
| 2011/0265889 A1* | 11/2011 | Tanaka | A61F 5/44 |
| | | | 137/386 |
| 2016/0310711 A1* | 10/2016 | Luxon | A61B 5/4839 |

* cited by examiner

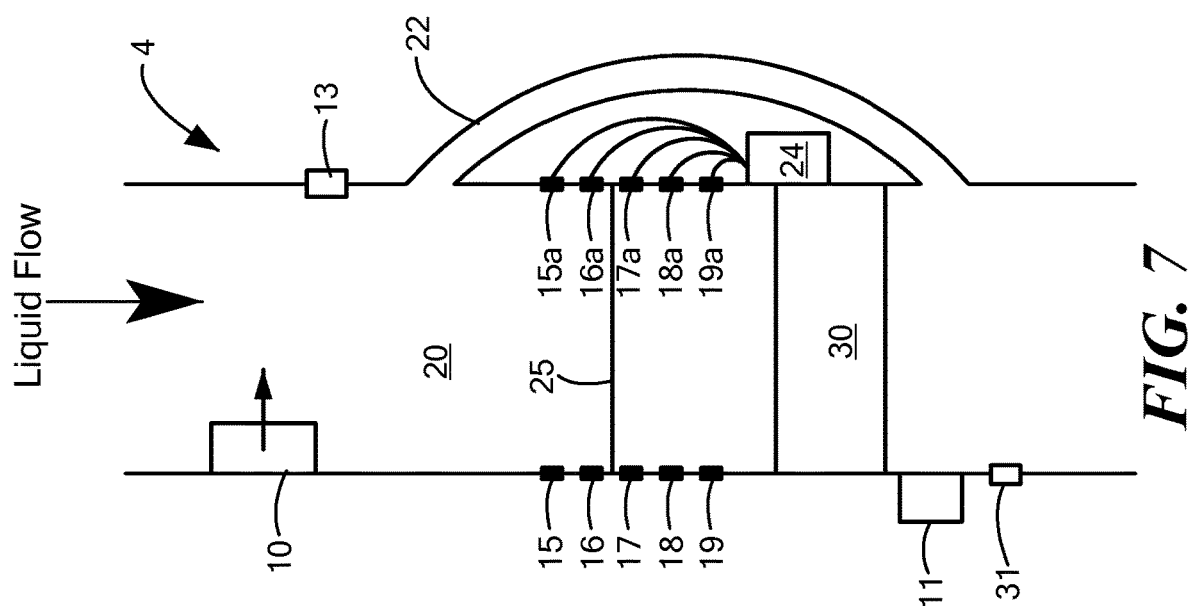
FIG. 7
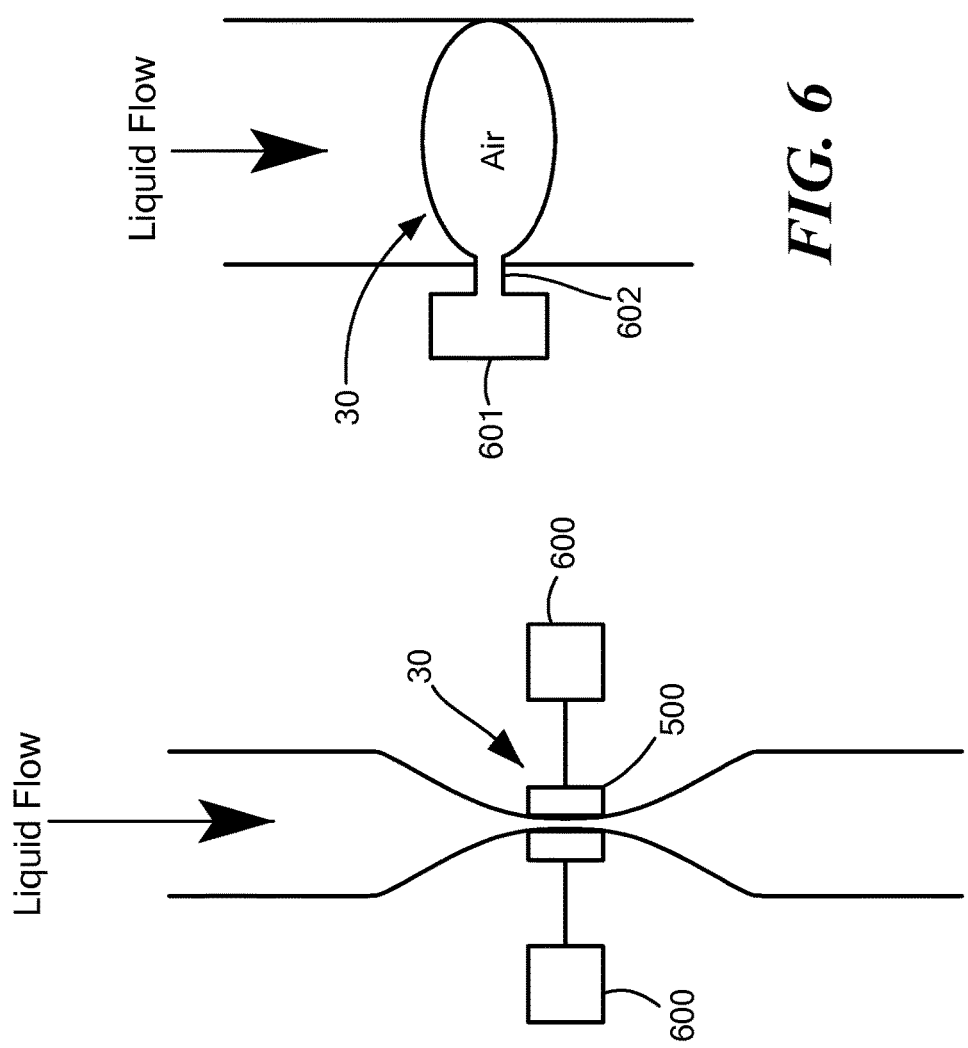
FIG. 6
FIG. 5

DEVICE AND METHOD FOR MONITORING IRREGULAR LIQUID FLOW RATES

This application claims the priority of U.S. Provisional Application No. 62/011,111 filed Jun. 12, 2014 and entitled "Fluid Output Measurement Device and Method", the whole of which is hereby incorporated by reference.

BACKGROUND

When the flow of liquid through a conduit such as a pipe or tubing is regular, the flow can be computed as the volume of liquid that has passed through the pipe of tubing in an unit time. However, measuring the flow rate of liquids through a pipe or tubing when the flow rate is low, irregular with time, and without external pressure or forces acting on it other than gravity, is challenging since the liquid doesn't fill the entire cross section of the pipe. This problem is further compounded when the pipe or tubing is free to be tilted or rotated along any of the three commonly used axes of symmetry in a Cartesian coordinate system. In addition it is frequently desirable that a flow measurement device can measure a range of flow rates including alternating high and low flow rates. Finally, while sophisticated and costly solutions to this problem may exist, in many areas including medicine it is paramount to achieve such measurements in the most cost-effective manner.

Currently, urine output in ICU patients is measured in hourly intervals (often in intervals of 4 hours) through a transparent, pliable plastic bag or container. Though suitable for some purposes, such an approach often does not meet the needs of users. For example, this method can be inaccurate, resulting in reduced detection of low urine output episodes. Also, ICU nurses can spend a significant amount of their time measuring and recording urine output, and these time-intensive tasks can result in inaccuracies and treatment errors. Further, failing to detect the complications of acute kidney injury (AKI) can lead to additional costs.

Thus, there remains a need for devices and methods that permit accurate, high resolution, and automated monitoring of liquid flow rates under such conditions.

SUMMARY OF THE INVENTION

The present invention is based on the premise is that under conditions of low and irregular flow with no external pressure, the flow rate through a conduit can be measured by periodically blocking the flow through the pipe or tubing via a blocking mechanism (i.e., a closure) such that a volume of the fluid accumulates in a measuring chamber or collection vessel, which may be the pipe or tubing itself. Measuring the amount of time required for accumulation of a predetermined volume of fluid allows computation of the volume of fluid passing through the tubing per unit time, i.e. the flow rate. In the limit when the volume of fluid measured is small the time elapsed would be small as well and the measured flow rate would approximate the instantaneous flow rate through the pipe or tubing, and the flow rate can be measured in real-time. The volume to be measured can be predetermined by a human operator of the device or it can be set automatically and changed dynamically over time by a computer algorithm that accounts for the past history of the flow rate of the liquid. The latter feature enables a range of flow rates to be measured using only one chamber retaining the fluid.

One aspect of the invention is a device for monitoring of an irregular liquid flow rate. The device includes a collection vessel having an inlet and an outlet, a liquid level sensor in the collection vessel, a closure, and a control unit. In embodiments of the device, only a single collection vessel or measurement chamber is present in the device. The collection vessel is configured to allow liquid to enter through the inlet and leave through the outlet, respectively. The closure opens and closes the outlet in response to signals from the control unit. The liquid level sensor provides a signal to the control unit when liquid in the vessel attains a first preset volume. The processor is programmed to open the valve to empty the vessel when the preset volume is attained and to determine a liquid flow rate based on the preset volume and the time required to reach the preset volume.

Another aspect of the invention is a liquid collection system that includes the device described above and a catheter for collecting liquid from the subject. The catheter is coupled to the inlet of the device by tubing. In some embodiments, the system also includes a liquid collection bag coupled to the outlet of the device by tubing.

Yet another aspect of the invention is a method of monitoring an irregular flow rate of liquid from a subject. The method includes the steps of: (a) providing the device described above whose inlet is connected to a catheter in the subject; (b) allowing liquid from the catheter to accumulate in the collection vessel of the device for a period of time until the first preset volume of liquid is reached; (c) measuring the period of time from beginning of liquid accumulation to reaching the first preset volume using the control unit; and (d) obtaining a liquid flow rate measurement from the quotient of the first preset volume and said period of time.

The invention can be further summarized by the following listing of items of the invention.

1. A device for monitoring of an irregular liquid flow rate, the device comprising a collection vessel having an inlet and an outlet, a liquid level sensor in the collection vessel, a closure, and a control unit; wherein the collection vessel is configured to allow liquid to enter through the inlet and leave through the outlet, respectively; wherein the closure opens and closes the outlet in response to signals from the control unit; wherein the liquid level sensor provides a signal to the control unit when liquid in the vessel attains a first preset volume; and wherein the processor is programmed to open the valve to empty the vessel when the preset volume is attained and to determine a liquid flow rate based on the preset volume and the time required to attain the preset volume.
2. The device of item 1, wherein the closure is opened by an operator in response to a prompt by the control unit.
3. The device of any one of the preceding items, comprising a plurality of liquid level sensors that are vertically distributed on an inside wall of the collection vessel, wherein the device is configured to function when disposed within 45 degrees of a vertical orientation.
4. The device of any one of the preceding items, further comprising a liquid bypass channel that diverts liquid from the collection vessel after a bypass preset volume has been attained.
5. The device of any one of the preceding items, further comprising an air vent in an upper portion of the collection vessel.
6. The device of any one of the preceding items, wherein the collection vessel is a rigid container or tube.
7. The device of any one of the preceding items, wherein the collection vessel is a flexible container or tube.

8. The device of any one of the preceding items, wherein the closure is a clamp or a valve.
9. The device of any one of the preceding items, wherein the first and/or bypass preset volume is user adjustable.
10. The device of any one of the preceding items, wherein the liquid level sensor is located on a central axis of the collection vessel.
11. The device of any one of the preceding items, wherein the liquid level sensor comprises a flotation member.
12. The device of any one of the preceding items, wherein the liquid level sensor measures the weight of liquid in the collection vessel.
13. The device of any one of the preceding items, wherein the liquid is urine collected from a subject by means of a catheter.
14. The device of any one of the preceding items, wherein the control unit comprises a processor, a memory, and a display.
15. The device of any one of the preceding items, wherein the control unit comprises a wireless transmitter.
16. The device of any one of the preceding items, wherein the control unit is programmed to alert a user if the liquid flow rate is outside of a predetermined range or if a predetermined flow rate pattern is observed.
17. A liquid collection system comprising the device of item 1 and a catheter for collecting liquid from the subject, the catheter coupled to the inlet of the device by tubing.
18. The system of item 17, further comprising a liquid collection bag coupled to the outlet of the device by tubing.
19. A method of monitoring an irregular flow rate of liquid from a subject, the method comprising the steps of:
   (a) providing the device of item 1 whose inlet is connected to a catheter in the subject;
   (b) allowing liquid from the catheter to accumulate in the collection vessel of the device for a period of time until the first preset volume of liquid is reached;
   (c) measuring the period of time from beginning of liquid accumulation to reaching the first preset volume using the control unit; and
   (d) obtaining a liquid flow rate measurement from the quotient of the first preset volume and said period of time.
20. The method of item 19, further comprising opening the closure of the device to empty the collection vessel, followed by repeating steps (b) through (d).
21. The method of any one of items 19-20, wherein the device comprises a plurality of liquid level sensors arranged in a vertical distribution within the collection vessel, and the flow rate is measured from the periods of time required for liquid to accumulate to the level of each sensor.
22. The method of any one of items 19-21, wherein the flow rate is determined periodically over time.
23. The method of item 22, wherein the device comprises a display, and the flow rate as a function of time is shown on the display.
24. The method of any one of items 19-23, wherein the device alerts a user when the measured flow rate is outside of a predetermined range or when a predetermined flow rate pattern is observed.

BRIEF DESCRIPTION OF THE DRAWINGS

FIG. 5 illustrates an external clamp fluid flow blocking and release mechanism (closure).

FIG. 6 depicts an inflatable closure that operates externally.

FIG. 7 depicts an exemplary measurement device in which the pipe or tubing serves as the collection vessel or measurement chamber.

The embodiments disclosed herein are not intended to limit or define the full capabilities or features of the device. The drawings and depictions constitute exemplary embodiments of the device and methods.

DETAILED DESCRIPTION OF THE INVENTION

The present invention provides devices and methods for the determination and monitoring of the flow rate of liquids through a conduit when the flow rate is low, irregular, and acted on only by the force of gravity, such as when bodily fluids are collected from a subject in a clinical setting. The premise is that under conditions of low and irregular flow with no external pressure, the flow rate through a tubing or fluid collection device may be measured by periodically blocking the flow through the conduit, via a blocking mechanism or closure such that a volume of the fluid accumulates in a measuring chamber or collection vessel, which may be the conduit itself or a parallel liquid pathway. Measuring a variable amount of time that is required for a fixed, pre-determined volume of fluid to accumulate allows computation of the volume of fluid per unit time, i.e. the flow rate, even if the flow rate is subject to large fluctuations over time. In the limit, when the volume of fluid measured is small the time elapsed would be small as well, and the measured flow rate would approximate the instantaneous flow rate through the pipe or tubing. The volume to be measured can be predetermined by a human operator of the device or it can be set to operate automatically and changed dynamically over time by a computer algorithm that accounts for the past history of the flow rate of the liquid. The latter feature would enable a range of flow rates to be measured using only one chamber or collection vessel retaining the fluid.

The volume of fluid accumulated may be determined by a wide variety of sensors that can measure the level of fluid in the measuring chamber. Equivalently, the volume may be determined by measuring the weight of the accumulated fluid and knowing its specific gravity by using any suitable sensors or scales known in the art. The volume and the time of the measurement can be recorded by a microprocessor, which then signals to a release mechanism (which may be but need to be the same as the closure or blocking mechanism) to open or unblock the pipe or tubing for a period of time sufficient to allow draining of the accumulated liquid. The liquid flow is then blocked again and the process can be repeated periodically to measure the flow rate through the pipe or tubing over time, such as for monitoring a fluid flow from a subject in a clinical setting.

Figure 1:
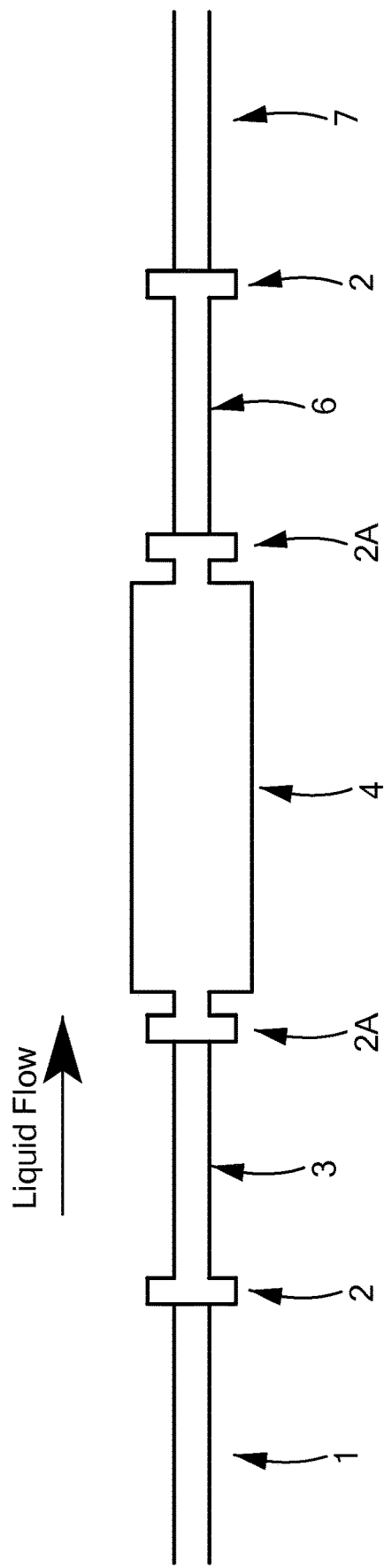
FIG. 1 is a schematic view of a portion of an embodiment of a measurement device in accordance with the invention.

FIG. 1 depicts an exemplary context in which a liquid measurement device will be used in accordance with various embodiments. The device 4 will be incorporated in-line within either flexible tubing or a rigid pipe having an input side 1 and an output side 7. The device may be coupled to the pipe or tubing using any suitable couplings or seals 2 and 2A known in the art. Optionally, the device may contain a portion of input pipe or tubing 3 and output pipe or tubing 6 that are an integral part of the device. The diameters of the various pipe or tubing components depicted in FIG. 1 are purely illustrative and it is explicitly understood that the pipes or tubing integral to the device may have equal, larger, or smaller diameter than the pipe or tubing it is inserted in.

Figure 2:
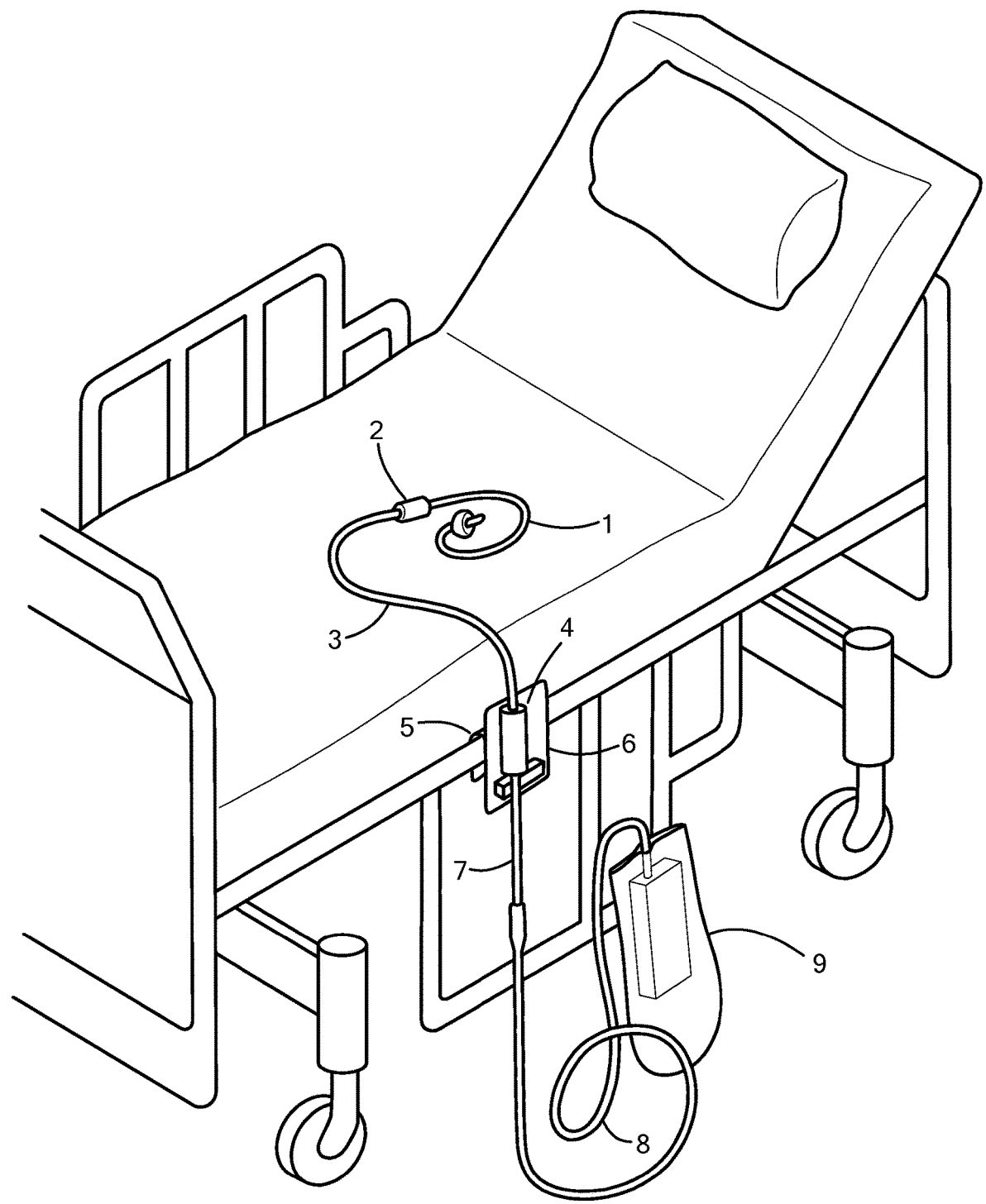
FIG. 2 is a schematic illustration of a liquid collection system of the invention in the context of a medical setting where urine flow from a catheterized patient is measured and collected.

In one medical application of the device, FIG. 2 displays a Foley catheter tubing 1 which inserts into the genital orifice and connects to the bladder (though other means of coupling to a body are contemplated as are appropriate in other given settings and applications) connects to an optionally larger tubing 3 that may be an integral part of the device disclosed herein. In other embodiments, the tubing may insert into other parts of the human body, orifices, or surgical sites to collect and measure body liquid output. There may be a sterile seal 2 surrounding the connection that can be perforated when relevant or necessary.

A liquid measurement device 4 may be inserted between the end of the catheter 1 and the collection container tubing 7, as shown in FIG. 2, where the catheter 1 can be a Foley catheter or another catheter, such as, but not limited to, a Jackson-Pratt drain, a pleural tube, or a cerebrospinal fluid tube. Liquid output generally passes in one direction through the liquid measurement device 4 from the catheter 1 through the device input tubing 3 into the device output tubing 6. In one embodiment, in inserting the liquid measurement device 4, the connection between the catheter 1 and the collection container tubing 7 is separated and the liquid measurement device 4 is manually inserted therebetween. The catheter 1 is then connected to an input tubing 3 of the liquid measurement device 4 and an output tubing 6 of the liquid measurement device 4 is connected to the collection container tubing 7.

With continued reference to FIG. 2, in one embodiment, collection container tubing 7 may be included or may be coupled to the output tubing of the device 6 by means of one or more suitable couplings and/or seals as are understood in the art. In some contexts, the tubing 7 may have bending and kinking 8, thus proving the need for more proximal measurements in order to mitigate measurement errors, such as liquid retention within the collection container tubing 7. Additionally, the proximal location of the liquid measurement device 4 to the liquid source improves flow rate calculations and increases the measurement accuracy.

In one embodiment, one or more portions or the entire liquid measurement device 4 are disposable. For example, portions of the liquid measurement device 4 that may or may not contact the liquid may be disposable while certain other portions not contacting the liquid may be non-disposable. In another embodiment, the entire device is disposable. In yet another embodiment, portions or the entirety of the liquid measurement device 4 may be included as part of a liquid output draining mechanism comprising of a Foley catheter set (or tray) or another drainage set, including, but not limited to, a Jackson-Pratt drain, a pleural tube, or a cerebrospinal fluid tube. By this, sterility can be maintained without having to manually insert the liquid measurement device 4.

Returning now to FIG. 2, the liquid measurement device 4 may include a hook 5 or place-guard allowing the liquid measurement device 4 to be anchored to a supporting structure. The hook 5 can be easily and securely affixed to any structure, platform, or cross-rail found commonly in the in-patient setting. One purpose of the hook 5 may be to minimize the potential orientations of the liquid measurement device 4. In various embodiments, the liquid measurement device 4 can be included with the tubing 3 and/or tubing 6 separate from the device, positioned at or near an end collection container 9, or attached as a separate add-on. It is understood that a collection container 9 may not be necessary in many applications outside of medicine and the measurement of bodily fluids.

Figure 3A:
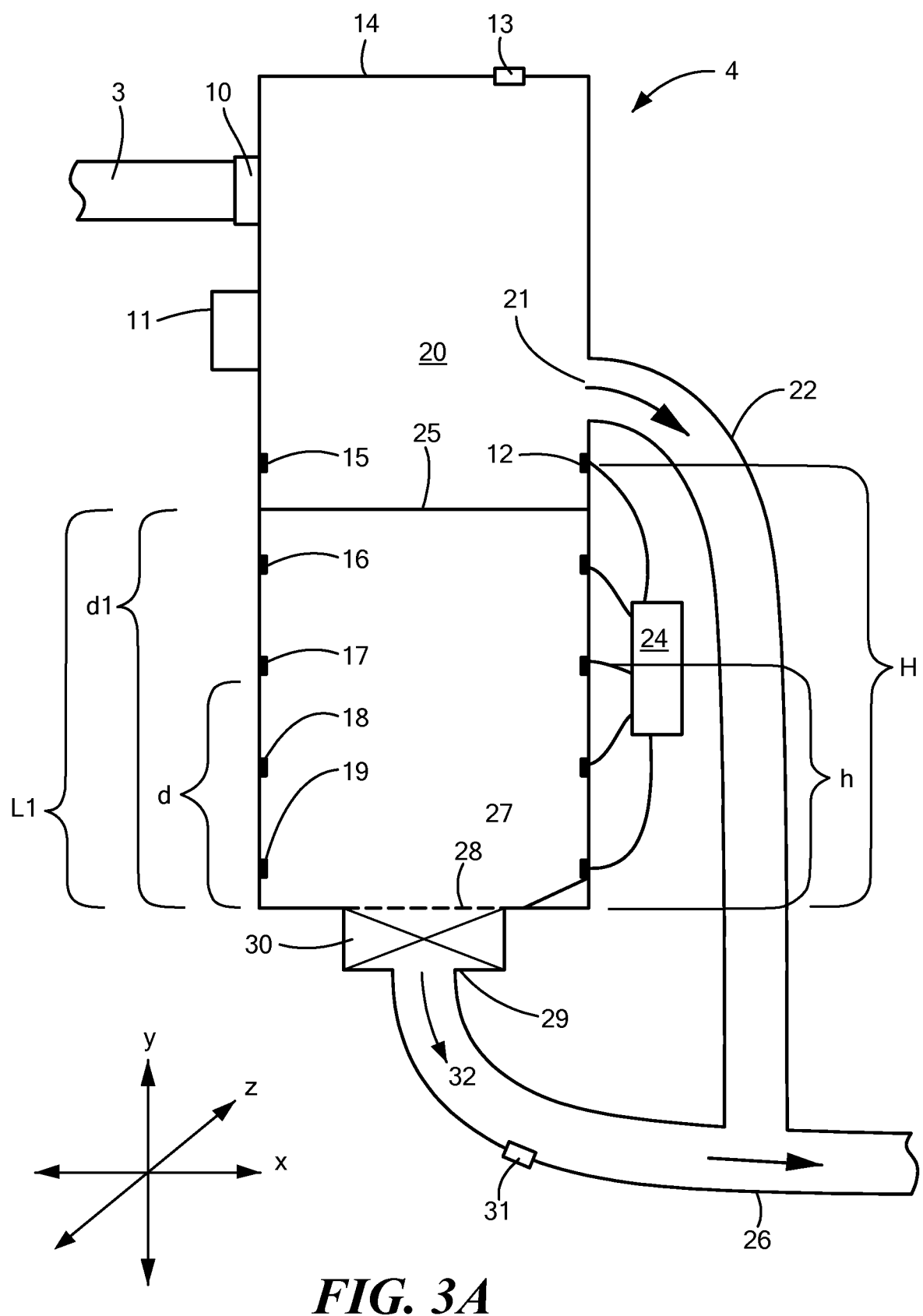
FIG. 3A is a schematic illustration of an exemplary measurement device in a vertical orientation.
Figure 3B:
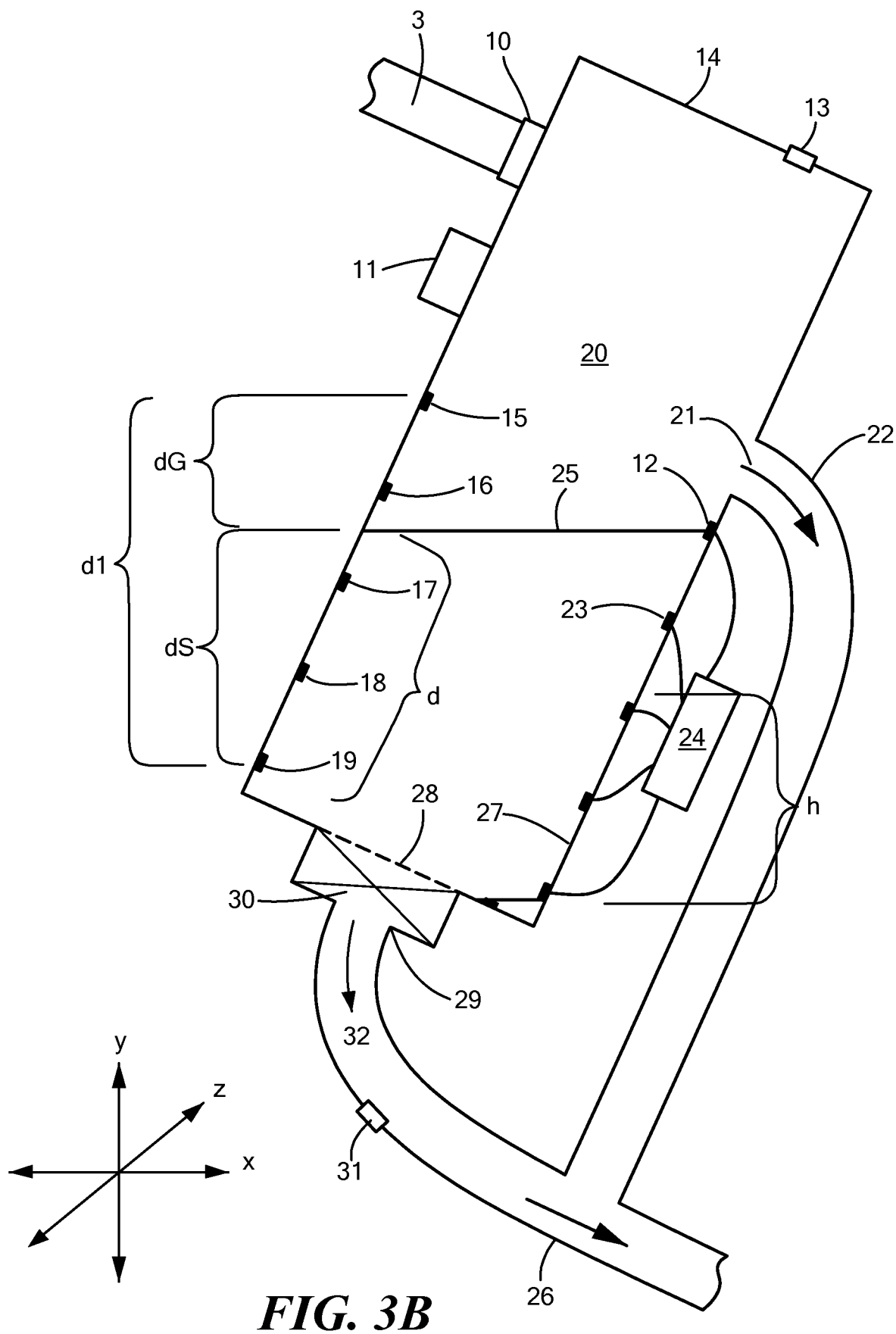
FIG. 3B is a schematic illustration of an exemplary measurement device showing its operation at an exemplary angle different from a vertical orientation.

Turning now to FIGS. 3A and 3B, a more detailed description of the liquid measurement device 4 is provided in accordance with various embodiments. Given the typical usage of liquid output collection and measurement devices in hospital environments it is desirable that the liquid measurement device 4 can operate accurately in a wide range of orientations as described by its rotation within a reference frame commonly described by the three axes of rotation x, y, and z. FIG. 3A shows an exemplary measurement device 4 in a vertical orientation while an exemplary non-vertical orientation is depicted in FIG. 3B. For clarity, it is beneficial to first describe how the device 4 operates in a strictly vertical orientation where its axes of symmetry are aligned with those of the reference coordinate frame. Referring to FIG. 3A, the device includes at least one chamber 20 (also referred to herein as a collection vessel or measurement chamber) with a liquid blocking and release mechanism 30 at the bottom. Liquid enters the device through the input tubing 3 which, in one embodiment, is an integral part of the device but need not be. When the fluid flow blocking and release mechanism 30 is in the closed position, liquid accumulates in the chamber 20 and its level begins to increase. In one embodiment, a series of sensors 15-19 (where the number of sensors in the series is purely exemplary) that are capable of detecting the presence of the liquid are aligned along the inside or outside surface of the chamber walls, or within the walls themselves. Once a sensor, for instance 17, at a certain height h from the bottom of the chamber senses the presence of liquid at that height, its state changes from "off" to "on," and the volume of the liquid in the chamber 20 can be readily computed by the controller 24 from the height h and the geometrical dimensions of the chamber; the time elapsed since the last time that the chamber was empty can also be recorded. The controller 24 may adjust the volume reading to account for meniscus formation based on the chamber geometry and readily available formulae. When the liquid level reaches the sensor 15 positioned farthest from the bottom of the chamber at a height H that sensor signals to the controller 24 that the maximum allowable capacity of the measurement device has been reached and the controller 24 in turn activates the opening of the fluid flow blocking and release mechanism 30 to release the liquid in the chamber 20.

In certain embodiments, only one sensor at a height H is sufficient to measure a certain pre-determined volume, however situating multiple sensors in a vertical line is advantageous as it allows a multiplicity of volumes to be measured and recorded independently of the release of the liquid from the chamber. In other embodiments, the sensor(s) may be situated in the geometrical middle of the chamber and attached to a support rod or tube, extending downwards from the top wall of the chamber. For example, in one embodiment, the liquid measurement device 4 may include a spout (not shown) that assists the liquid that enters into the device from the input tubing 3 to collect at the bottom of the chamber 20, and the sensor(s) described herein may be attached on the spout. Any other support structure or structures for attachment of the sensors that may be known in the art may be used within the chamber 20 in any orientation. FIG. 3A demonstrates one particular embodiment of heights H and h, respectively.

Referring additionally to FIG. 3B, we now consider the operation of the device when it is tilted at an exemplary orientation from the vertical position as depicted in FIG. 3A. First, we note that if the sensor (or series of sensors 15-19) is/are situated at the exact geometrical middle of the chamber 20 and the chamber is rigid with a symmetrical shape, then at any tilt of the chamber along the axes x, y, and z the level of the liquid in the chamber at those sensor(s) locations will not change if the rotation is slow and/or when the system equilibrates at the new orientation. Therefore, with such a placement of the sensor(s) the device would be able to measure and record the volume of liquid in the chamber at a wide range of orientations without sacrificing accuracy.

If the sensor(s) are placed on or along the walls of the chamber then additional sensors and computations are necessary to determine the volume of the liquid. This is most easily achieved by placing identically positioned vertical lines of sensors in a symmetrical fashion along opposing walls of the chamber such that there are pairs or quadruples of sensors at the same distance (or height if the device is vertical) from the bottom of the chamber. While only two rows of sensors are depicted in FIG. 3B capturing changes in orientation around the y-axis, it is understood that such rows of sensors will be placed on the other two opposing walls of the chamber (not shown) in order to capture changes in orientation around the x-axis. If the device is in vertical orientation as shown in FIG. 3A with the liquid at a certain level L1 then the four sensors at a corresponding distance d1 (where h/d and H/D coincide in this position) from the bottom of the chamber should each be signaling the presence of the liquid to the controller 24, thus, providing an error check for the device.

Further, each of the sensors situated at distances d from the bottom of the chamber that are less than d1, as seen in FIG. 3A, should also signal presence of the liquid, thereby building in additional error checking capabilities.

When the device is tilted at an orientation different from vertical then the pairs (or quadruples if the tilt is along more than one axis) of sensors at the same distance d from the bottom of the chamber will no longer be sensing the presence of liquid in the chamber simultaneously. In FIG. 3B, as an example, the two sensors at the same distance d, or paired sensors, would be sensor 12 and sensor 15. Instead, as depicted by the line in FIG. 3B representing the liquid level 25, and as an illustrative example, if the sensor 23 on the right side of the device at the greatest distance DM=D from the bottom of the chamber is sensing presence of the liquid, one or more of the sensors 15-19 on the left side may remain above the liquid level. Therefore a certain sensor on the left hand side at a distance d1 from the bottom of the chamber will be sensing the presence of the liquid such that all sensors in the left-side series at greater distances dG do not signal presence of the liquid, while all sensors at smaller distances dS signal its presence, as exemplified in FIG. 3B.

The controller 24 processes and records periodically the state of each of the sensors, and, in the exemplary situation described above, determines that the maximum allowable liquid level has been reached with respect to the right side of the chamber and signals to the fluid flow blocking and release mechanism 30 to release the liquid while at the same time computing a volume VT which would be smaller than the volume VM when the device is fully vertical. The volume VT is readily computed from the geometry of the device and from the angle of the tilt. In this example, the tilt angle is in turn determined by 1) the offset in the number of sensors between the top sensor on the right side and the corresponding highest activated sensor on the left side, and 2) the spacing between the sensors.

While FIG. 3B exemplifies only one angle along one axis at which the device may be tilted it is understood that similar principles of the volume computations apply when the device is oriented at different angles and along two axes and the volumes can be computed by readily available geometrical formulae embedded as software in the controller 24 in one embodiment. It is noteworthy that rotation around the z-axis does not impact the level of the liquid in the device and therefore does not influence the volume calculations.

The fluid flow blocking and release mechanism 30 can be opened and/or closed by a signal from the controller 24 at either fixed intervals or variable intervals determined by a pre-defined calculation and/or a defined function. As the mechanism 30 opens, the measured and analyzed liquid is released. The controller 24 is configured to control when the blocking and release mechanism 30 will open, close, and for how long, as well as calibrate the measurements and analysis. Once all the liquid is released, the status of the sensors is changed back to the "off" state. The fluid flow blocking and release mechanism 30 can be opened, held open, and closed through mechanical stimulus, electrical stimulus, magnetic stimulus, or any other suitable known method or combination thereof. In one embodiment, the mechanism may be a solenoid valve. The duration of the valve opening, the rate of opening and closing, and other mechanical factors related to the measurement and analysis accuracy can be adjusted in real-time depending on the volume of liquid to be released from the device.

In another embodiment, depicted in FIG. 5 the fluid flow blocking and release mechanism 30 is an automated or manual pressure clamp 500 which is located outside of the tubing. The clamp blocks the liquid flow by applying appropriate pressure to the tubing and opens the tubing to release the liquid by relaxing that pressure.

In yet another embodiment shown in FIG. 6 the fluid blocking and release mechanism 30 may consist of a compartment 600 that is inflatable with air manually or through a pump 601 from the outside such that when the compartment is fully inflated the flow of liquid through the pipe or tubing is completely blocked representing the "closed" state of the release mechanism, whereas when the compartment is fully deflated the flow of liquid through the pipe or tubing is completely unrestricted and representing the "open" state of the release mechanism. Intermediate states between the "open" and "closed" states can be effectuated by intermediate degrees of inflation of the compartment, which would have the effect of varying the diameter of the tubing or pipe and restricting the flow of the liquid through them.

In yet another embodiment shown in FIG. 7, the device may not need a vessel or chamber to collect the liquid being measured, as once the liquid flow is stopped by the liquid flow blocking and release mechanism 30 the liquid may accumulate in the pipe or tubing itself. The volume of fluid accumulated may then be measured by the sensors 15-19 as described above, including the capacitive sensors described below, that can be placed on the internal surface of the pipe or tubing itself. Knowing the geometrical configuration of the tubing and the distance between the sensors and the liquid flow blocking and release mechanism 30 would allow measurement of the volume of liquid accumulated at a wide range of angles and orientations without the need of arranging the sensors is corresponding pairs equidistant from the mechanism 30.

In one embodiment, as shown in FIG. 3B, there may exist an additional flow blocking mechanism 10 on the input side to the liquid measurement device 4 that prevents liquid from entering into the chamber 20 while the fluid flow blocking and release mechanism 30 is opened to release the measured liquid. The additional blocking mechanism 10 helps prevent or limit unmeasured liquid from passing through the device while the measured liquid is being released. It can be similar to the mechanism 30 on the output side of the device or can be another traditional valve or a stop-gap mechanism functioning as a liquid place holder while the fluid flow blocking and release mechanism 30 remains open.

In one embodiment, the flow blocking mechanism is contained within the chamber 20 itself (not shown), and separates the bottom part of the chamber where the measurements of the liquid volume and other liquid properties occur, from the upper part of the chamber. In yet other embodiments, the flow blocking mechanism may prevent or limit back flow of liquid toward the input tubing 3 when the device is tilted at extreme angles regardless of whether the fluid flow blocking and release mechanism 30 is open.

In one embodiment, a release mechanism 11 (not shown) may exist on the external surface of the chamber 20 that allows manual release of liquid from the chamber 20 by setting and adjusting the fluid flow blocking and release mechanism 30 in an open position. The release mechanism 11 may employ a button, switch, lever, pull-out piston or any other suitable mechanical mechanism known in the art. Additionally, the release mechanism 11 may coordinate measurement of liquid output at discrete time intervals that are clinically necessary to optimize real-time decision making for patient care. The manual release mechanism may operate both the release mechanism 30 and the additional blocking mechanism 10 mechanically without requiring external power. Upon activating the release mechanism 11, and prior to release of the liquid, an automatic measurement may be generated by coordinating the opening of the release mechanism 30 with reading of the status of the sensors prior to the opening of mechanism 30 via the controller 24.

In another embodiment, liquid release and measurement cycles are automated and coordinated by software embedded in the controller 24. For example, in one implementation, measurements and release of liquid may occur simultaneously at discrete time intervals set at times clinically relevant for real-time clinical decision making. These time intervals may be defaulted to reflect national standards of optimal measurement intervals or may be set per the specific clinical caretaker's preferences given appropriately documented clinical need for such a change.

Figure 8:
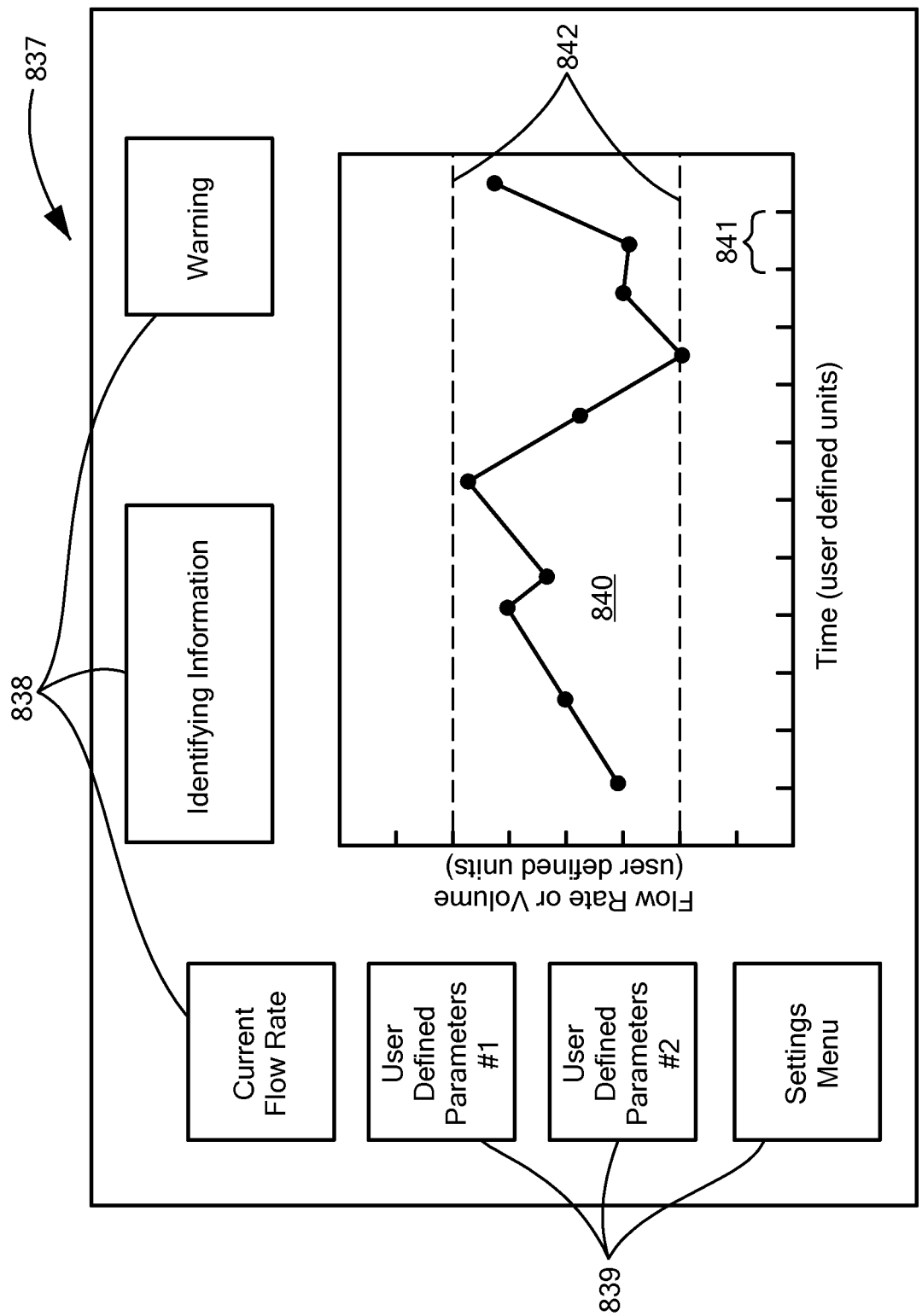
FIG. 8 is an illustration of an exemplary software application display for a control unit of a liquid flow monitoring device of the invention.

Patients in the clinical setting may present a wide range of liquid outputs around what is considered the normal output as normalized for body weight, or another clinical parameter. For example, whereas some may have oliguria associated with very low rates of urine output, others may have polyuria which is associated with excessively high levels of urine output. The difference between the low and high urine outputs may be as high as one hundred fold. Therefore, it is desirable that the disclosed device 4 can operate not only at a wide range of orientations but also at a wide range of flow rates. Thus, in another embodiment, the liquid level measurement and liquid release intervals while still simultaneous may be increased or reduced automatically depending on the increased or decreased rates of liquid output observed from the filling rate of the chamber 20 or by the prior time intervals of liquid release. The controller 24 also communicates the time intervals and the volumes (or other properties of the liquid) measured at those time intervals to software for processing and display such as depicted in FIG. 8.

In one embodiment, the disclosed liquid measurement device 4 is designed so that the measurement of the liquid volume, and other liquid properties, does not need to be simultaneous with the release of the liquid from the device. By using a multiplicity of sensors communicating with the controller in the manner described above, very frequent measurements of the liquid volume (or other liquid properties) can be recorded along with the times when a given volume (or other liquid property) was measured, thereby enabling computations of the liquid flow rates (or the rates associated with other liquid properties). The release intervals of the liquid from the chamber, however, need not be simultaneous with those of the measurement intervals and may be considerably longer. Uncoupling the liquid measurement and release intervals allows for dynamical adjustments of the collected volume of liquid in the device depending on the rate of liquid inflow and thus enables a single chamber with a fixed volume to measure liquid output at both low and high flow rates. Therefore, unlike other prior art measurement techniques the disclosed device does not need two or more separate chambers or a multiplicity of liquid chambers within chambers to enable the measurement process. In addition, uncoupling the liquid measurement from its release allows for more efficient management of the power requirements, if necessary, to operate the fluid flow blocking and release mechanism 30.

The disclosed liquid measurement device 4 does not require any active pumping or movement of the liquid and only requires the passive inflow of liquid to complete measurements. Additionally, the presently disclosed liquid measurement device 4 may not require a counterweight, or information on additional liquid movement, gravitational restraints beyond ensuring passive liquid movement, heat exchange, or thermal dissipation.

In one embodiment, the sensors 15-19 are capacitive sensors. One or more sensors 15-19 may be incorporated in a thin, flexible circuit to accommodate a curved surface of the chamber. Alternatively, one or more sensors 15-19 may be embedded on a traditional printed circuit board (PCB) for mounting on a flat surface. The sensors include embedded software which can be configured either for auto-calibration for ease of use or manual calibration to maximize the accuracy.

Figure 3C:
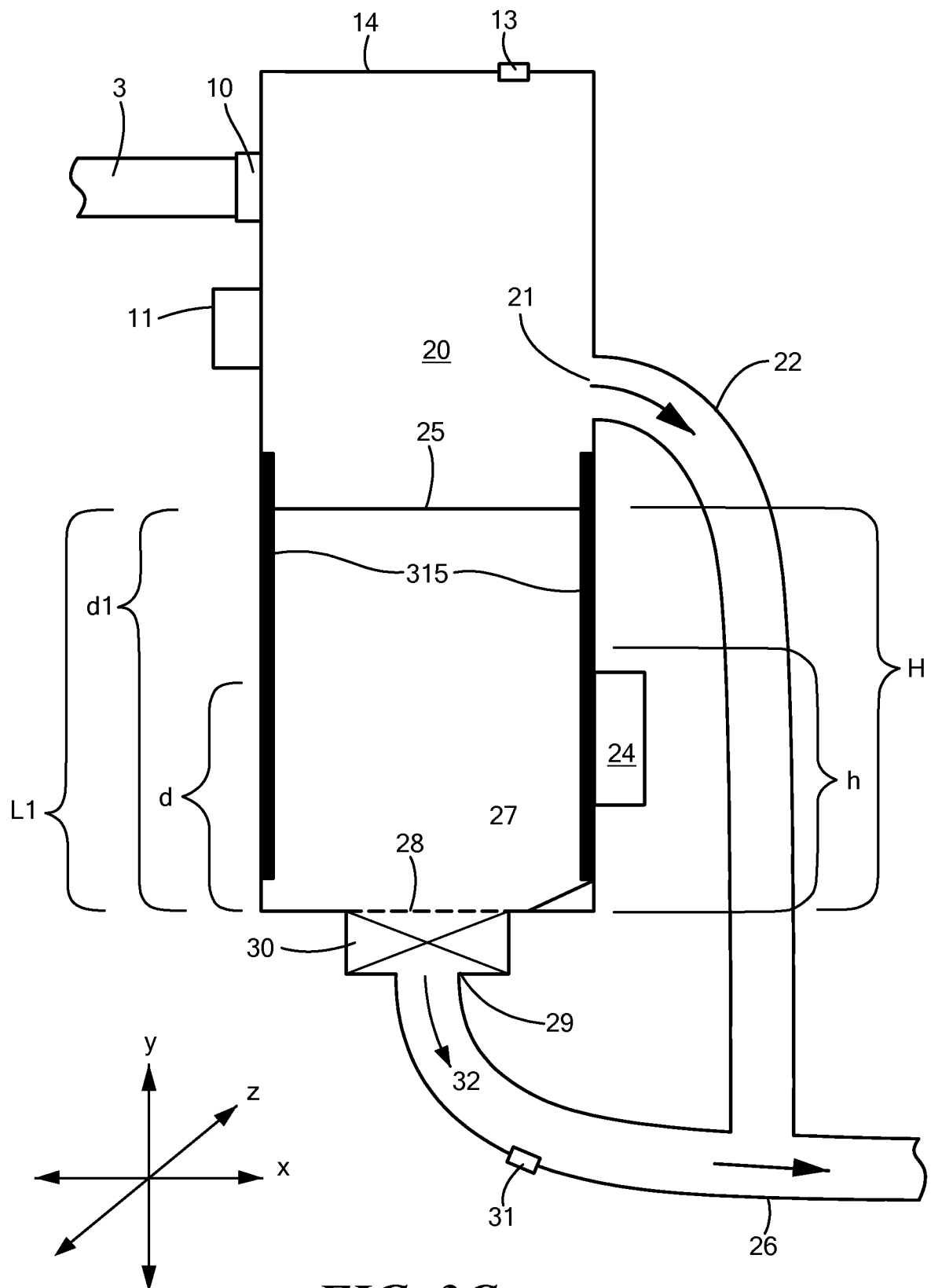
FIG. 3C represents an embodiment of the measurement device that uses continuous sensors instead of an array of sensors.
Figure 4:
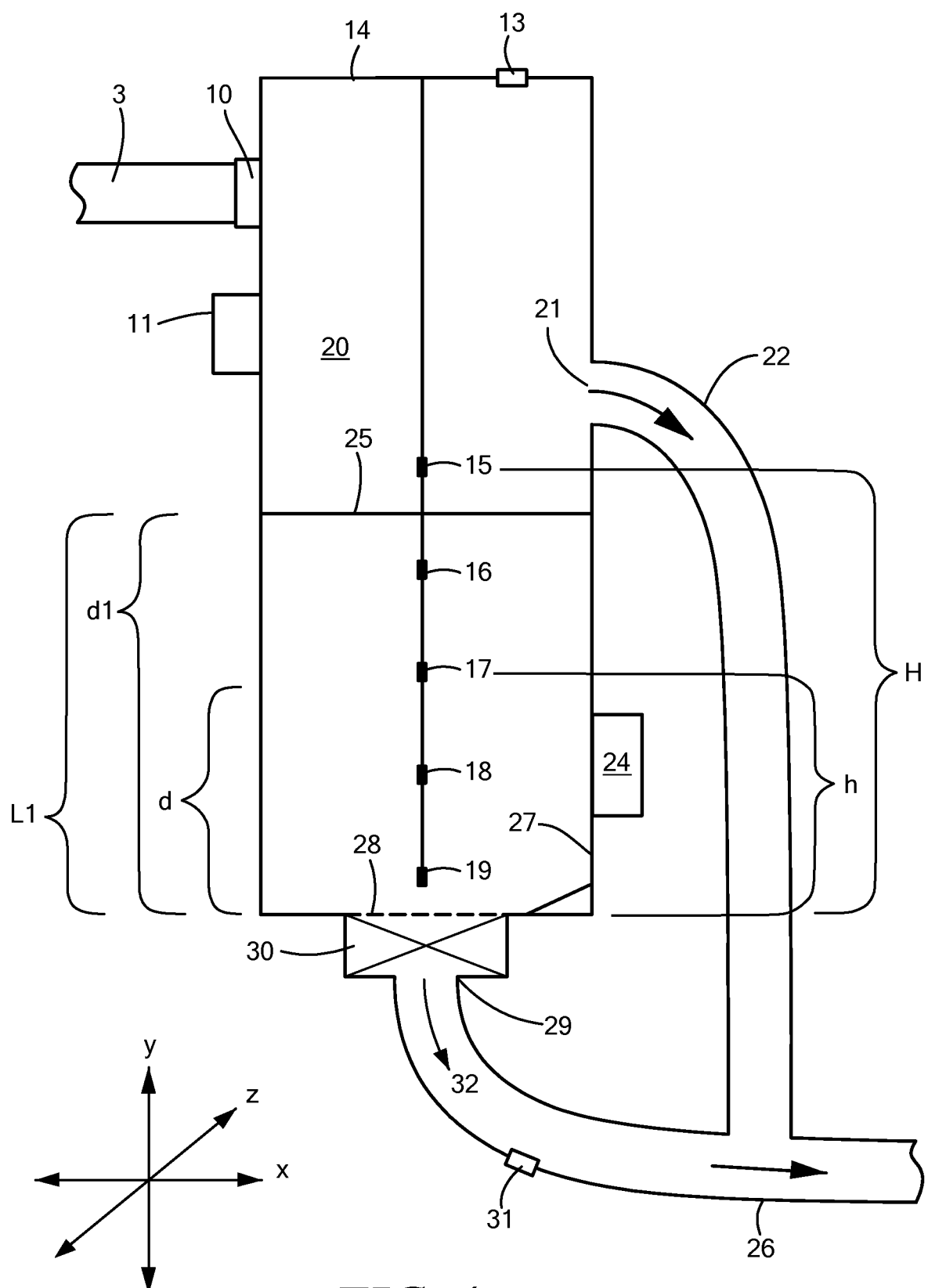
FIG. 4 illustrates an embodiment of the measurement device with the sensor(s) placed in the geometrical middle.

In another embodiment depicted in FIG. 3C. there are single continuous sensors 315 instead of each of the vertical arrays of sensors described above such that the level of the liquid present in the chamber can be determined by the length of the sensor that is submerged in the liquid due to the change in resistive, conductive, or capacitive properties of the sensors 315.

While one exemplary embodiment for the placement of the sensors 15-19 is described with reference to FIGS. 3A and 3B, the sensors 15-19 can be arranged in multiple patterns defined by any mathematical functions. The sensors may be arranged in a manner to optimize the accuracy of the measurements or to optimize the cost of manufacturing, including using the fewest sensors possible. The size, orientation, and/or proximity of the sensors are intended to minimize error from measurements. For instance, two possible sources of error from the placement of the sensors are: the distance between the sensors and the size of the sensors. The sensors 15-19 may be positioned in very close proximity to minimize errors due to liquid in the space between two successive sensors remaining unaccounted. Additionally, the focus of the sensor placement and patterns may not be to increase the accuracy of all measurements, but to increase the accuracy of a set of measurements, within a defined range, and/or at fixed volumes. By setting baseline values of optimal measurement ranges, optimal measurement intervals are achieved as opposed to optimal measurements overall. One or more sensors can be placed in the tubing 3 proximal to the chamber 20 or in the tubing 6 distal to the chamber 20, or on the bypass channel 22 (described below) of the chamber 20.

Various embodiments may incorporate multiple sensor types into the liquid measurement device 4. These sensors can detect, measure, and analyze relevant information from the liquid, including, without limitation, information related to total volume, rate, solute concentration, analyte, compound, temperature, density, and/or opacity. Information obtained from the sensors may correlate to other clinical data as well. For example, sensors placed within the chamber 20 or on the outer surface of the chamber 20 may detect clinically relevant information about the liquid output, including the volume, rate, concentration, analyte presence, temperature, density, and/or opacity. Sensors may include, without limitation, one or more resistive, capacitive, ultrasound, and/or thermal sensors, or any combination thereof.

With continued reference to FIG. 3B, other aspects are described. In addition to measuring and analyzing the liquid output, sensors may be incorporated that independently monitor the orientation of the liquid measurement device 4 and that can detect rapid motions such as jerking motions or other random movements. For example, accelerometers may be used outside of the chamber 20 to detect such aberrant motions and transmit this information to the controller so that appropriate error control algorithms can be applied in order to reduce or eliminate the influence of sudden motions on the sensor states and, therefore, volume calculations. Further, the sensors 15-19 may be capable of differentiating readings that are due to aberrant motion of liquid within the chamber 20 relative to actual filling differences by introducing a suitable time lapse between sensing the liquid and signaling an "on" state to the controller 24.

Integral to the liquid measurement device 4 there may be one or more air vents, such as two air vents 13 and 31, that serve to regulate the pressure in the system by eliminating or reducing positive pressure ("back pressure") events as well as negative pressure ("suction") events, further improving device capabilities and allowing for faster release of the measured liquid from the device. The air vents 13 and 31 allow air to escape the device to prevent back pressure events and air to enter into the device to prevent suction events. The vents may be any suitable vents known in the art and, in one embodiment, have a plastic inner membrane that will not wet-out during use. The membrane also acts as a bacterial and viral barrier with greater than 99.99% efficiency.

In one embodiment, the second air vent 31 prevents or limits air locks that may render the device inoperable or slow down the rate of release of liquid from the device. The airlocks may be created by static pockets of liquid in the tubing 7 which may form from time to time when the tubing bends or kinks 8 as a result of the positioning of tubing and/or the collection container 9. The second air vent 31 can enhance the rate of exit of the liquid from the chamber 20 into the distally located output channel 32, device output tubing 6, and collection container tubing 7 in cases where an airlock has formed.

In one embodiment, the liquid measurement device 4 includes a bypass channel 22 incorporated to prevent backflow into the catheter 1 whether due to a sudden excess output of the liquid from the patient that exceeds the available free volume of the chamber or due to malfunction of the device. In case of device malfunction, the bypass channel 22 allows liquid to escape to the collection tubing 7 and container 9 in order to prevent backflow of liquid into the catheter or bladder or liquid accumulation that may cause infections. Liquid can also enter the bypass channel 22 through outlet 21 if the device is tilted to an extreme orientation which then reconnects with the output channel 32 distal to the device at the connector 26.

An outlet 29 of the liquid measurement device 4 through the fluid flow blocking and release mechanism 30, the output channel 32 and into the distal output tubing 6 can be shaped in a manner to prevent or limit stasis of liquid and designed to minimize measurement error in the device. In one embodiment, a width of the distal output channel 32 is set at a specific diameter to minimize an opening time of the fluid flow blocking and release mechanism 30 and ensure complete, rapid evacuation of the liquid. The ratio of a diameter of the distal output channel 32 relative to the mechanism 30 can be a function of the opening time required of the mechanism 30. Restraints on the channel diameter may be partially or wholly based on the chamber geometry. The bypass channel 22 and the distal output channel 32 connect within the liquid measurement device 4 in order to maintain the direction of the liquid flow downstream from the device and towards the collection container 9, if such is necessary.

The combination of air vents and the bypass channel minimizes or eliminates liquid retention in the device and/or backflow into the Foley catheter 1 that may be conducive for infections. The chamber 20 may be designed with a shape that facilitates complete draining of the liquid, for example narrowing or tapering near the bottom. In addition, the liquid measurement device 4 may include a suitable bactericidal coating 14 or other coating as is known in the art to prevent infection risks.

While both certain embodiments and exemplary embodiments have been described above and many equivalents, alternatives, variations, and modifications, aside from those expressly stated, are possible and within the scope of the disclosure, additional embodiments of the device can be described as follows. In one embodiment, the chamber 20 has a volume in the range of 5 milliliters (ml) to 100 ml and the device 4 is able to measure volumes in the range of 1 ml to 50 ml. The size of the device, in one embodiment, is 1 inch (in) to 5 inches in the maximum dimension with a larger dimension along the vertical axis than along the other two axes in order to minimize measurement errors. In one embodiment, the tubing 3 containing the measurement device with the catheter 1 has a length of 12 inches to 24 inches in order to accommodate patient movement in the bed without the exercise of tension or sudden pulling on the device.

In one embodiment, the liquid measurement device 4 measures one or more biomarkers including, but not limited to, biomarkers that may be indicative of clinical inflammatory responses, lack of responses, clinically significant reactions, or clinically important information. For example, for urine output, a clinical response, AKI would be detected by sensors indicating biomarkers such as, but not limited to, uNGAL, pNGAL, KIM-1, pCyc, and IL-18. Biosensors that analyze components within the liquid can have associated immunoassays, analyzing the presence and/or concentration of a particular substance, compound, molecule, or complex analyte within the liquid. The liquid measurement device 4 may include an immunoassay unit or module in which measurement and analysis can take place and be recorded. These analytes hold relevant information that impact real-time decision making and/or overall informational analysis specific to the liquid. Biosensors may detect particular molecules, particulates, and/or any clinically relevant organic-based substance within the liquid that identifies important information about the kidney function, for example, and about the overall body function, including, without limitation, cardiac, pulmonary, oncologic, lymphatic, hematological, neurologic, gastrointestinal, hepatobiliary, musculoskeletal, general inflammatory, immunologic conditions, or any combination of these and/or other conditions. Biosensors can be located on the inner surface, within, or outside of the chamber 20. Biosensors can multiplex and coordinate information regarding analyte concentration, presence, and any changes thereof, and can communicate with a sentinel sensor or microcontroller or display information directly. Liquid output values can be correlated with values and trends in critical biomarkers to enable analysis of liquid output with biomarker values to identify critical trends, ratios, and rates to impact clinical decision making.

In one embodiment, corrosion of the sensors 15-19 and the fluid flow blocking and release mechanism 30 can be prevented by an anti-corrosive coating 27 along the inner surface of the liquid measurement device 4. This coating 27 will not impact overall measurements or analysis. Additionally, sensors can be placed on the external surface of the liquid measurement device or embedded in its walls preventing the need for a corrosive-resistant coating.

Additionally, material within the liquid that may precipitate can be collected and siphoned distally toward the collection container 9. The liquid measurement device 4 can be designed specifically to prevent sediments 28 from the liquid to collect and aggregate at the lower portion of the liquid measurement device 4 through the chamber design and the fluid flow blocking and release mechanism orientation and design. Additionally, a coating can be included around the output aspect of the chamber 20 and the mechanism 30 to further prevent accumulations that can impact device function or measurement accuracy. The shape, contours, and design specifications of the chamber can be adjusted to optimize liquid with varying viscosities, output rates, and other important liquid characteristics.

The liquid measurement device 4 may communicate, via cable or a wireless connection, with one or more software programs that may be configured to display the liquid properties. These display units may be independent consoles, integrate into telemetric display, integrate into an existing computer network, or be displayed upon the device 4 itself. Turning now to FIG. 8, an exemplary screenshot 837 of such a display is illustrated.

The screenshot 837 shown on FIG. 8 can be exhibited on a separate display or integrated within a larger display screen enabling data presentation alongside other any other parameters. For example, a dedicated display can be included on or coupled to the liquid measurement device 4. However, the liquid measurement device 4 may also be connected to a larger system (such as a computer network, patient care network, electronic medical or health record, a telemetric network, or any secure computer server) and will enable display of the pertinent data within a separate window of, for example, a computer display.

The information 838 reported may include the current flow rate per user defined time interval with exemplary time intervals that can be adjusted from time to time based upon input from an operator. Various display time intervals such as total interval length and/or relative interval length can be managed by input located on the module itself or peripherally, for example, from a centralized database, centralized control, or other remote control, which may include a similar visual format as depicted in FIG. 8.

Additional information 839 regarding the fluid flow of fluid properties may be reported. This may include the total liquid volume that has passed through the pipe or tubing since an initial point of time (or during a specified time interval), or the rate of change in liquid flow rate, or other liquid properties calculated by the disclosed measurement device 4. The flow rate as a function of time can be displayed as data points 940 that may be or may not be independent of the time of the periodic volume release of the liquid and the measurement interval per release and may be calculated and visualized at discrete time intervals 841 that can be either be defaulted to intervals meaningful for the particular application of the device or chosen at the discretion of an operator. The data points 840 shown in FIG. 9 may encompass all data points accrued, or may limit information to only more recent data points displayed as a rolling window graph, and/or a rolling or moving average. The software may include an upper limit and/or a lower limit (together 842) for the flow rate and can alert the operator if the current flow rate values fall outside of that range.

Many of the functional units described in this specification have been labeled as modules, devices, software, or other discrete nomenclature in order to more particularly emphasize their implementation independence. For example, a module may be implemented as a hardware circuit comprising custom VLSI circuits or gate arrays, off-the-shelf semiconductors such as logic chips, transistors, or other discrete components. A module or software may be implemented in programmable hardware devices such as field programmable gate arrays, programmable array logic, programmable logic devices or the like.

Modules may also be implemented in software for execution by various types of processors. An identified module of executable code or other portions of software may, for instance, comprise one or more physical or logical blocks of computer instructions that may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, software or a module of executable code could be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

The data collected may reference only the flow rate or a ratio or relationship between the liquid flow rate and another parameter measured by the device, such as a biomarker.

As used herein, "consisting essentially of" does not exclude materials or steps that do not materially affect the basic and novel characteristics of the claim. Any recitation herein of the term "comprising", particularly in a description of components of a composition or in a description of elements of a device, can be exchanged with "consisting essentially of" or "consisting of".

While the present invention has been described in conjunction with certain preferred embodiments, one of ordinary skill, after reading the foregoing specification, will be able to effect various changes, substitutions of equivalents, and other alterations to the compositions and methods set forth herein.

The invention claimed is:

1. A device for monitoring of an irregular liquid flow rate, the device comprising a single collection vessel having a volume in the range from 5 mL to 100 mL and having an inlet and an outlet, a plurality of liquid level sensors that are vertically distributed on an inside wall of said collection vessel when the device is in a vertical position, a closure, and a control unit; wherein the device is configured to monitor an irregular flow rate when tilted at any angle within a range of 45 degrees of a vertical orientation as well as when vertical; wherein the collection vessel is configured to allow liquid to enter through the inlet and leave through the outlet, respectively; wherein the closure opens and closes the outlet in response to signals from the control unit; wherein one of the plurality of the liquid level sensors provides a signal to the control unit when liquid in the vessel attains a first preset volume; and wherein the processor is programmed to open the valve to empty the vessel when the first preset volume is attained and to determine a liquid flow rate based on the first preset volume and the time required to attain the first preset volume.

2. The device of claim 1, wherein the closure is opened by an operator in response to a prompt by the control unit.

3. The device of claim 1, further comprising a liquid bypass channel that diverts liquid from the collection vessel after a bypass preset volume has been attained.

4. The device of claim 1, further comprising an air vent in an upper portion of the collection vessel.

5. The device of claim 1, wherein the collection vessel is a rigid container or tube.

6. The device of claim 1, wherein the collection vessel is a flexible container or tube.

7. The device of claim 1, wherein the closure is a clamp or a valve.

8. The device of claim 1, wherein the first and/or bypass preset volume is user adjustable.

9. The device of claim 1, wherein the plurality of liquid level sensors are located on a central axis of the collection vessel.

10. The device of claim 1, wherein the plurality of liquid level sensors comprise a flotation member.

11. The device of claim 1, wherein the plurality of liquid level sensors measure the weight of liquid in the collection vessel.

12. The device of claim 1, wherein the liquid is urine collected from a subject by means of a catheter.

13. The device of claim 1, wherein the control unit comprises a processor, a memory, and a display.

14. The device of claim 1, wherein the control unit comprises a wireless transmitter.

15. The device of claim 1, wherein the control unit is programmed to alert a user if the liquid flow rate is outside of a predetermined range or if a predetermined flow rate pattern is observed.

16. A liquid collection system comprising the device of claim 1 and a catheter for collecting liquid from the subject, the catheter coupled to the inlet of the device by tubing.

17. The system of claim 16, further comprising a liquid collection bag coupled to the outlet of the device by tubing.

18. A method of monitoring an irregular flow rate of liquid from a subject, the method comprising the steps of: (a) providing the device of claim 1 whose inlet is connected to a catheter in the subject; (b) allowing liquid from the catheter to accumulate in the collection vessel of the device for a period of time until the first preset volume of liquid is reached; (c) measuring the period of time from beginning of liquid accumulation to reaching the first preset volume using the control unit; and (d) obtaining a liquid flow rate measurement by dividing the first preset volume and said period of time.

19. The method of claim 18, further comprising opening the closure of the device to empty the collection vessel, followed by repeating steps (b) through (d).

20. The method of claim 18, wherein the flow rate is measured from the periods of time required for liquid to accumulate to the level of each one of said plurality of liquid level sensors.

21. The method of claim 18, wherein the flow rate is determined periodically over time.

22. The method of claim 21, wherein the device comprises a display, and the flow rate as a function of time is shown on the display.

23. The method of claim 21, wherein the device alerts a user when the measured flow rate is outside of a predetermined range or when a predetermined flow rate pattern is observed.

* * * * *